United States Patent [19]

Scripps et al.

[11] 4,018,888

[45] Apr. 19, 1977

[54] AMINE-STABILIZED DRY POWDER AEROSOL ANTIPERSPIRANT COMPOSITIONS AND METHOD OF PREPARATION

[75] Inventors: Charles L. Scripps, Springfield Township, Hamilton County; Jerry J. Yetter, Green Township, Hamilton County, both of Ohio

[73] Assignee: The Procter & Gamble Company, Cincinnati, Ohio

[22] Filed: Aug. 11, 1971

[21] Appl. No.: 170,970

Related U.S. Application Data

[63] Continuation-in-part of Ser. No. 888,959, Dec. 29, 1969, abandoned.

[52] U.S. Cl. .................................................. 424/47
[51] Int. Cl.² ........................ A61K 7/34; A61K 7/38
[58] Field of Search .................. 424/46, 47, 66, 68

[56] References Cited

UNITED STATES PATENTS

| | | | |
|---|---|---|---|
| 2,230,082 | 1/1941 | Montenier | 424/68 |
| 2,890,987 | 6/1959 | Hilfen | 424/68 |
| 3,288,681 | 11/1966 | Goldberg et al. | 424/47 |

Primary Examiner—Dale R. Ore
Attorney, Agent, or Firm—Robert B. Aylor; Ronald L. Hemingway; George W. Allen

[57] ABSTRACT

Dry powder antiperspirant compounds are suspended in aerosol compositions by means of $C_{12}$–$C_{20}$ primary aliphatic amines to prevent agglomeration or packing of the antiperspirant compounds in the aerosol container. The compositions are prepared by first dissolving and then precipitating the amines in the presence of the antiperspirant compounds.

4 Claims, No Drawings

Ser. No. 888,959 filed

AMINE-STABILIZED DRY POWDER AEROSOL ANTIPERSPIRANT COMPOSITIONS AND METHOD OF PREPARATION

CROSS-REFERENCE TO RELATED APPLICATION

This application is a continuation-in-part application of our copending application Ser. No. 888,959 filed Dec. 29, 1969 now abandoned entitled "AMINE-STABILIZED DRY POWDER AEROSOL ANTIPERSPIRANT COMPOSITIONS AND METHOD OF PREPARATION."

BACKGROUND OF THE INVENTION

1. Field of the Invention

Antiperspirant compositions in the form of aqueous lotions, creams, and sticks have been known in the art for many years. More recently aerosols under pressure have become prominent as a means of application to the skin. Among aerosols, it is especially preferred to suspend the antiperspirant compound as a dry, impalpable powder in a nonaqueous liquified propellant form. Such a product applies the antiperspirant salt effectively to the skin and feels dry, smooth, and comfortable. Furthermore, because the antiperspirant compound is not dissolved it is not corrosive to ordinary metal aerosol cans and it is therefore not necessary to use especially lined cans or breakable glass bottles, both of which are expensive.

Typically such a composition contains one or more metallic, acidic astringent salts as antiperspirant compound; i.e., for perspiration control. A suspending agent is employed to keep the antiperspirant compound from agglomerating or settling out and packing tightly at the bottom of the aerosol container. A carrier liquid is added so that the stream issuing from the aerosol container is moist spray which adheres to the skin rather than a dusty cloud. Minor adjuvants are optional, such as antimicrobial compound and perfume.

2. Prior Art

Certain dry aerosol antiperspirant compositions have been disclosed in the patent literature; for example, Netherlands Pat. No. 66/13943 granted to Spitzer et al on Apr. 4, 1968; U.S. Pat. No. 3,288,681 granted to Goldberg et al on Nov. 29, 1966; and British Pat. No. 987,301 granted to Shulton, Inc. on Mar. 24, 1965.

SUMMARY OF THE INVENTION

It has been newly discovered that certain amines are highly effective agents for the purpose of suspending dry antiperspirant compounds in aerosol compositions which comprise:

a. From about 2% to about 12% by weight of a finely divided dry antiperspirant powder;

b. from about 0.2% to about 1% by weight of a suspending agent for the antiperspirant powder comprising a primary aliphatic amine having from about 12 to about 20 carbon atoms;

c. from about 3% to about 15% by weight of a non-toxic, non-aqueous carrier liquid of low volatility having emollient properties; and d. an anhydrous, non-toxic liquefiable propellant gas under pressure in an amount sufficient to produce an aerosol spray.

DETAILS OF THE INVENTION

Components of the Antiperspirant Formulation

Component a

Antiperspirant compounds suitable for use in this invention can be any of those known in the art that are insoluble in the aerosol composition as a whole. These are acidic, metallic salts, often of aluminum, zirconium, or zinc. Probably aluminum chlorhydroxide is the most widely used astringent salt though many others are also suitable: Aluminum chloride, aluminum sulfate, aluminum oxychloride, aluminum oxysulfate, zirconyl hydroxy chloride, zirconium oxychloride, zinc sulfate and zinc sulfocarbolate. In addition to these simple salts, many inorganic/organic mixtures and complexes have been suggested as antiperspirant compounds. Among these are zirconium salt/amine/amino acid complexes as taught by Siegal et al. in U.S. Pat. No. 3,407,254 (Oct. 22, 1968), e.g., complexes of the formula:

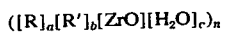

in which:

1. R is a nucleophilic compound,
2. R' is an amino acid compound,
3. n is a number of from 1 to 32 inclusive, and corresponds to the number of zirconium atoms in the molecules of the complex,
4. a is a number of from 1 to 5 inclusive,
5. b is a number of from 1 to 5 inclusive,
6. c is a number from 0 to 4 inclusive,
7. a+b+c has a value of from 2 to 6 inclusive, and
8. wherein R, R', $H_2O$ and O, when present, are attached directly to Zr;

zirconium salt/aluminum chlorhydroxide/glycol complexes as taught by Jones et al. in U.S. Pat. No. 3,405,153 (Oct. 8, 1968), e.g., inorganic-organic complexes having the formula:

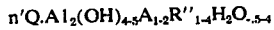

wherein Q is a member of the group consisting of zinc chloride, zinc iodide, zinc bromide, zinc hydroxy chloride, zinc hydroxy iodide, zinc hydroxy bromide, zirconyl chloride, and zirconyl hydroxy chloride; A is an anion selected from the group consisting of chloride, bromide and iodide; R'' is the coordinating moiety of a polyhydroxy compound having at least two carbon atoms to which are attached at least two hydroxy groups, and n' is the number of moles of Q and is at least 0.05; aluminum chlorhydroxide/glycol complexes as taught by Jones et al. in U.S. Pat. No. 3,420,932 (Jan. 7, 1969), e.g., complexes having the formula:

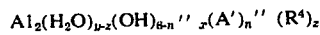

wherein A' is selected from the class consistng of chloride, bromide, iodide, sulfate and sulfamate; $R^4$ is the coordinating moiety of a polyhydroxy compound having a carbon chain in which at least two carbon atoms link a hydroxyl group to said chain, n'' is a positive integer of from 1 to 4; x is the valence of A', y is a value of about 0.5 to 6 and is always such that (y–z) does not give a negative value; and z is the number of available coordinating sites, with n''x being from 2 to 4; zirconyl and aluminum halohydroxy complexes as taught by Beekman in U.S. Pat. No. 2,906,668 (Sept. 29, 1959), e.g., complexes having the formula:

$ZrOCl_2Al_{n'''}(OH)_{n'''(2-2.5)}(Cl)_{n(0.5-1)}$ in which $n'''$ is a number within the range 2–10 and the numbers of OH groups and Cl atoms are so selected, within the ranges stated, that their total will be $3n'''$; aluminum-zirconium complexes as disclosed in the copending application of Raymond E. Bolich, Jr., Ser. No. 59,690 filed July 30, 1970 entitled "ALUMINUM-ZIRCONIUM AEROSOL ANTIPERSPIRANT COMPOSITION AND PROCESS," e.g., a complex prepared by:

A. Heating an aqueous solution containing from about 1 to about 3.2 parts of aluminum chlorhydroxide to a temperature of from about 190° F. to about 225° F.;

B. Adding an aqueous solution containing 1 part zirconyl hydroxychloride ratewise to the aluminum chlorhydroxide solution over a period of from about 2 hours to about 5 hours while heating and agitating, the total solids content at this point being at least about 10%; and C. Heating and agitating the aluminum chlorhydroxidezirconyl hydroxychloride mixture at a temperature of from about 190° F. to about 225° F. for from about ½ hour to about 5 hours until a stable complex forms.; and aluminum and zirconium hyddroxychloride complexes as disclosed in the copending application of Wilmer L. Luedders et al., Ser. No. 130,833 filed Apr. 2, 1971 entitled "DRY POWDER AEROSOL ANTIPERSPIRANT COMPOSITION INCORPORATING DRY POWDER ANTIPERSPIRANT ACTIVE COMPLEX AND PROCESS FOR ITS PREPARATION," e.g., complexes prepared by:

A. Co-dissolving in water
1. one part $Al_2(OH)_{6-m}X_m$, wherein X is an anion selected from the group consisting of chloride, bromide and iodide and m is an integer from about 0.8 to about 1.2;
2. $n^4$ parts ZrY wherein Y is an anion selected from the group consisting of —0(OH)Cl and $OCl_2$, and where $n^4$ has a value of from about 0.16 to about 1.2;
3. p parts neutral amino acid selected from the group consisting of glycine, dl-tryptophane, dl-$\beta$-phenylalanine, dl-valine, dl-methionine and $\beta$-alanine, and where p has a value of from about 0.06 to about .53;

B. Co-drying the resultant mixture at a temperature of from about 100° F. to about 230° F. to a moisture level of from about 0.5% to about 15% by weight; and C. Comminuting the resultant dried inorganic-organic antiperspirant complex into the form of an impalpable powder.

These patents and applications are incorporated herein by reference.

As mentioned supra, the antiperspirant compound is dispersed in finely-divided, powder form. The particle size of this compound must be small enough to remain suspended in the composition within the aerosol container, to pass through the valve without clogging, to disperse on the skin to provide adequate coverage, and to react rapidly enough with the moisture of the skin and air to convert the antiperspirant compound in dry powder form into the ionic state which is needed for effectiveness in suppressing perspiration.

Particle sizes smaller than about 100 microns are suitable for the practice of this invention, with particles averaging from about 10 microns to about 25 microns being preferred. The amount of antiperspirant compound is also governed by normal factors. Between about 2% and about 12% by weight of the composition is suitable for perspiration control for an aerosol burst of the duration the consumer is wont to use. Below about 2% the antiperspirant effectiveness drops off. Above about 12% is not practical because the antiperspirant effectiveness does not increase commensurate with additional quantities used; and in addition viscosity of the product increases so that handling is more difficult and atomization is less satisfactory. Preferred usage is from about 2.5% to about 6%.

Component b

The newly-discovered suspending agent of this invention is an amine. Suitable amines are those recited supra in the Summary of the Invention. Especially preferred are straight chain saturated primary amines, particularly hexadecyl amine and octadecyl amine. In general the effective amines of the instant invention are solid, not liquid, at room temperature.

The amines defined above unexpenctedly keep the aforementioned finely-divided powdered antiperspirant compound suspended in the composition as a whole. The antiperspirant does not settle to the bottom of the aerosol container and pack tightly into a compact solid mass nor does it clump or coagulate into large agglomerates that cannot be dispersed and dispensed with substantial uniformity.

From about 0.2% to about 1% of these amines by weight of the composition are suitable for the practice of the instant invention. At least 0.2% is required to accomplish the suspending function of this component. With amines that are relatively low in chain length, i.e., having 12 or 14 carbon atoms, solubility in the composition is increased and amounts somewhat higher than 0.2% are required. More than 1% is not required to perform the suspending function. In addition, excessive amounts of this component increase the viscosity of the composition which adversely affects ease of handling and atomization. Preferred usage of the amines of the instant invention is from about 0.3% to about 0.8% with from about 0.4% to about 0.7% by weight of the composition being especially preferred.

Without intending to be bound by theory, an explanation of the mechanism whereby amines perform the stabilizing function may be suggested. It has been observed that in the absence of antiperspirant compound [i.e., with only propellant, amine, carrier, and perhaps optional components present] the amine is not compatible with the rest of the formulation and forms a separate liquid layer. This layer does not occur when the antiperspirant compound is present. It is believed that in the latter situation the amine is strongly adsorbed onto the surface of the powdered antiperspirant compound, coating it and thereby preventing immediate contact between adjacent discrete antiperspirant particles which in turn prevents agglomeration and tight packing.

Component c

A carrier liquid of low volatility is used in the instant invention so that the stream issuing from the aerosol container is a moist spray rather than a gritty, dusty cloud. This imparts a cosmetic feeling to the skin when applied thereto and reduces the likelihood of breathing the otherwise dry powder. The carrier liquid also aids efficacy by keeping the antiperspirant compound in contact with the skin so that it does not flake off or wash off. Thus the carrier liquid is needed for practical use of the instant invention though it is not required per se for purposes of preparing a dry powder antiperspirant composition is stable form.

Any of the carrier liquids that are known in the art are suitable for the compositions of the instant invention. Examples are: Lanolin and fractions of lanolin such as those prepared by the teachings of U.S. Pat. No. 2,758,125, e.g., Lantrol, either as themselves or as their derivatives such as acetylated lanolin alcohols, e.g., Acetol prepared and refined according to U.S. Pat. No. 3,272,851, ethoxylated lanolin alcohols ethoxylated with from 1 to about 40 moles of ethylene oxide, hydrogenated lanolin alcohols such as Hydroxyol, lanolin fatty acids esterified with lower ($C_1$–$C_4$) fatty alcohols such as Isopropyl Lanolate; silicone oils such as polysiloxanes having the formula [—$R_2^5$Si O—]$_n$ where $R^5$ can be $C_1$–$C_4$ alkyl, phenyl, carboxyalkyl, etc., and the polysiloxane can have a viscosity at 25° C. of from about 5 to about 2,000 centistokes; Fluid AP; polyalkylene glycols which can contain a fatty acid or fatty alcohol group containing from about 2 to about 20 carbon atoms such as polyethylene glycol monolaurate and butoxy-polyoxyethylene oxypropylene glycols [The Ucon 50 HB series; Trade Mark - Union Carbide]; fatty alcohols containing from about 12 to about 18 carbon atoms such as lauryl, myristyl, hexadecyl, octadecyl, and oleyl alcohols; fatty acid esters of aliphatic alcohols where said esters contain from about 12 to about 26 carbon atoms such as ethyl laurate, isopropyl myristate, isopropyl palmitate, isopropyl behenate, decyl acetate, behenyl butyrate, hexadecyl acetate, decyl decanoate, methyl oleate, lauryl laurate, and oleyl acetate; aliphatic hydrocarbons such as mineral oil having a specific gravity at 60° F. of from about 0.8 to about 0.9 and aliphatic hydrocarbons containing from about 12 to about 26 carbon atoms such as tetradecane, hexadecane, nonane, tetracosane, etc.; esters containing multiple ester groups such as those disclosed in the copending application of Wilmer L. Luedders, Ser. No. 59,694 filed July 30, 1970 entitled "IMPROVED EMOLLIENTS FOR PARTICULATE ALUMINUM", i.e., a multiple ester organic compound of from about 12 to about 16 carbon atoms having a ratio of ester groups to carbon atoms of from about 0.125 to about 0.214 and having a solubility in water of from about 0.0005% to about 0.1% at 30° C., examples being di-n-octyl-n-decyl phthalate, di-n-octyl phthalate, di-n-hexyl phthalate, di-n-butyl phthalate, diethyl sebacate, diisopropyl adipate, and ethyl ethylcarbomethyl phthalate [ortho $C_2H_5$OOC-$\phi$-COOCH$_2$COOC$_2$H$_5$].

Still other operable carrier liquids are even more hydrophilic than these esters. Among them are polyethylene glycol monolaurate and butoxy-polyoxyethylene oxypropylene glycols [the Ucon 50 HB series; Trade Mark - Union Carbide].

Among these various carrier liquids, carboxylic esters having from about 12 to about 26 carbon atoms are preferred. As described supra, they can be either aliphatic or aromatic and can contain either one ester group or multiple ester groups. Especially preferred are di-n-butyl phthalate, diethyl sebacate, diisopropyl adipate, and ethyl ethylcarbomethyl phthalate.

Any of the carrier liquids described supra can be used in amounts from about 3% to about 15%. Below about 3% the carrier liquid is insufficient to form a moist spray and the spray is, therefore, undesirably dusty and gritty and does not adhere well to the skin. Above about 15% the composition deposited upon the skin feels undesirably oil and greasy. Amounts of carrier liquid from about 6% to about 10 % are preferred.

Component d

The propellant gas of the instant invention can be any liquifiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, propane, butane, 1,1-difluoroethane, 1,1-difluoro-1-chloroethane, dichloromonofluoromethane, methylene chloride, and isobutane, used singly or admixed. Trichlorofluoromethane, dichlorodifluoromethane, dichlorotetrafluoroethane, and isobutane, used singly or admixed, are preferred.

The amount of the propellant gas is governed by normal factors as well known in the aerosol art. It is satisfactory to consider the propellant as constituting the balance of the composition of the instant invention that is not accounted for by the other components as detailed herein. The preferred limits of propellant are therefore from about 70.7% to about 93.9%. Especially preferred limits are from about 80% to about 92%.

Component e.

Minor ingredients commonly used in the art are optional. Perfumes are one such ingredient, used in amounts up to about 0.8% by weight. Another is an antimicrobial compound, such as hexachlorophene, trichlorocarbanilide, trifluoromethyl carbanilide, and tribromosalicylanilide. Antimicrobials are used in amounts up to about 0.5% by weight to inhibit bacterial action upon perspiration and thereby reduce the resultant odors.

PROCESSING

The essential elements of the process of the instant invention are
i. Form a solution by dissolving component (b) in component (c) or component (d) or a mixture thereof;
ii. Mix component (a) into said solution; and
iii. Precipitate component (b). Step (i) can be accomplished by dissolving the amine, component (b), at about 110° to 150° F. in the carrier liquid, component (c), or in a propellant having an atomic ratio of chlorine to fluorine from about 2 to about 3 in which the amine is relatively soluble, as for example in CCl$_3$F or CCl$_2$FCCl$_2$F. A mixture of carrier liquid and propellant of this type is also suitable as a solvent for component (b) and in this case, the lower temperatures mentioned above are preferred. It is also preferred that the temperatures not be greatly in excess of the melting point of the particular amine used. Thus, for $C_{12}$ to $C_{14}$ amines the preferred temperatures are about 110°–130° F.; for $C_{18}$ to $C_{20}$ amines the preferred temperatures are about 130°–150° F.

Step (ii) can be done concurrently with step (i) or separately if desired.

Step (iii) can be accomplished by cooling to about 30°–80° F. Alternatively it can be done by adding a propellant having an atomic ratio of chlorine to fluorine from about 0.5 to about 1 in which the amine is relatively insoluble, as for example CCl$_2$F$_2$ or CHClF$_2$.

TESTING OF THE COMPOSITIONS

Compositions of the instant invention were tested for stability of the suspension by filling glass aerosol containers, storing at temperatures from 140° to 20° F. for periods ranging from one month to 12 months, respectively, and examining for separation and ability to redisperse. Color and odor were observed. Compositions were similarly stored at various temperatures for various times in commercial aerosol cans and examined for can corrosion, lining deterioration, absence of clogging in the valve, and satisfactory spray rates and patterns therefrom. Human subjects judged whether the deposit of the spray upon their skin was aesthetically pleasing. The compositions were also examined for their mildness.

In the Examples to follow, the properties supra will be referred to as "general physical properties."

Effectiveness of perspiration control was determined on human subjects by percent reduction in sweat for a treated, as compared with an untreated, axilla.

SPECIFIC EMBODIMENTS OF THE INVENTION

EXAMPLE I

Seventy-eight and three-tenths grams of $CCl_3F$, the propellant; 5.0 gm. of isopropyl myristate and 5.0 gm. of Acetulan (trademark, American Cholesterol Products, Inc. for acetylated lanolin), mixed carrier liquids; and 10.0 gm. of aluminum chlorhydroxide, the antiperspirant compound; were charged into a vessel. One and two-tenths grams of tetradecyl amine, the suspending agent, and 0.5 gm. perfume were added; the container was capped and shaken vigorously. The suspension was transferred to an aerosol container, 100 gm. $CCl_2F_2$ was added by cold fill, and the container was sealed. It was heated to 140° F. in a hot tank for five minutes and allowed to cool. General physical properties were tested and found to be good. The composition was an effective antiperspirant.

A comparable formulation was prepared wherein 5.0 gm. isopropyl myristate replaced the 5.0 gm. Acetulan. General physical properties were found to be good. Antiperspirant effectiveness is also good.

EXAMPLE II

One hundred twenty grams of $CCl_3F$, 12.0 gm. isopropyl myristate, and 12.0 gm. aluminum chlorhydroxide were charged into a vessel. One and three-tenths grams of hexadecyl amine was added; the container was capped and the concentrate therein was shaken vigorously. The suspension was transferred to an aerosol container, 145 gm. $CCl_2F_2$ was added by cold fill, and the container was sealed. General physical properties were found to be good, and antiperspirant effectiveness is good.

A comparable formulation was prepared wherein 1.3 gm. octadecyl amine replaced hexadecyl amine. General physical properties were found to be good and antiperspirant effectiveness is good.

The formulation of Example II is processed as above except that the concentrate contains octadecyl amine instead of hexadecyl amine; is heated to 150° F.; and subsequently is cooled to 80° F. All characteristics of the resultant composition are substantially the same.

The formulation of Example II is processed as above except that the concentrate contains tetradecyl amine instead of hexadecyl amine; is heated to 110° F.; and subsequently is cooled to 30° F. All characteristics of the resultant composition are substantially the same.

The formulation of Example II is processed by mixing together the isopropyl myristate and hexadecyl amine at a temperature of 130° F.; adding the aluminum chlorhydroxide and mixing again; cooling to 60° F.; then adding the propellants $CCl_3F$ and $CCl_2F_2$ and sealing in an aerosol container. All characteristics of the resultant composition are substantially the same.

The formulation of Example II is processed by mixing together the $CCl_3F$ and hexadecyl amine at a temperature of 80° F.; adding the aluminum chlorhydroxide and mixing again; then adding the isopropyl myristate and $CCl_2F_2$ and sealing in an aerosol container. All characteristics of the resultant composition are substantially the same.

EXAMPLE III

Compositions are prepared by the method of Example I, as follows where the numbers represent percent by weight:

|  | a | b | c | d |
|---|---|---|---|---|
| Aluminum chlorhydroxide | 5.0 | 2.0 | 12.0 | 4.0 |
| Lauryl amine | 1.0 | — | — | 0.3 |
| Eicosyl amine | — | 0.2 | 0.5 | 0.3 |
| Isopropyl myristate | 3.0 | 15.0 | 12.0 | 6.0 |
| Trichlorocarbanilide | 0 | 0 | 0.1 | 0.5 |
| Perfume | 0 | 0.4 | 0.8 | 0.4 |
| Propellant-$CCl_3F$:$CCl_2F_2$::60:40 weight ratio | 91.0 | 82.4 | 74.6 | 88.5 |
|  | 100.0 | 100.0 | 100.0 | 100.0 |

General physical properties and antiperspirant effectiveness are good.

The aluminum chlorhydroxide of Example III-a is replaced by aluminum chloride, aluminum sulfate, aluminum oxychloride, aluminum oxysulfate, zirconyl hydroxy chloride, zirconium oxychloride, zinc sulfate and zinc carbolate. Also complexes of zirconium salt-/amine/amino acid, zirconium salt/aluminum chlorhydroxide/glycol, and aluminum chlorhydroxide/glycol. In each case good general physical properties and antiperspirant effectiveness is exhibited.

The trichlorocarbanilide of Example III-c is replaced with hexachlorophene, trifluoromethyl carbanilide, and tribromosalicylanilide. General physical properties and antiperspirant effectiveness are substantially the same as for Example III-c.

The propellant mixture of Example III-d is replaced with 1,1-difluoroethane, 1-chloro-1,1-difluoroethane, dichloromonofluoromethane, methylene chloride, methyl chloroform, vinyl fluoride, vinylidene fluoride, trichlorofluoromethane, dichlorodifluoromethane, dichlorotetrafluoroethane, monochlorodifluoromethane, trichlorotrifluoroethane, propane, butane, and isobutane. General physical properties and antiperspirant effectiveness are good.

The isopropyl myristate of Example III-d is replaced with isopropyl palmitate, mineral oil, tetradecane, di-n- butyl phthalate, diisopropyl adipate, n-octyl-n-decyl phthalate, di-n-octyl phthalate, di-n-hexyl phthalate, lauryl alcohol, hexadecyl alcohol, oleyl alcohol, dimethyl polysiloxane having a specific viscosity at 25° C. of 350 centistokes, lanolin, Acetol, lanolin alcohols ethoxylated with about 5 moles of ethylene oxide, Hydroxyol, isopropyl ester of lanolin fatty acids, Fluid AP, polyethylene glycol (2.5 moles) monolaurate, butoxypolyoxyethylene (5.0) oxypropylene (5.0) glycol, myristyl alcohol, octadecyl alcohol, 3-ethyl-dodecyl alcohol, isopropyl myristate, isopropyl behenate, decyl acetate, ethyl laurate, behenyl acetate, hexadecyl acetate, decyl decanoate, methyl oleate, lauryl laurate, oleyl acetate, hexadecane, nonane, tetracosane, and mineral oil having a specific viscosity of about 0.865. General physical properties and antiperspirant effectiveness are good.

The same process is used to prepare compositions identical to those of Example III except that 24 grams of dibutyl phthalate are replaced by 24 grams of isopropyl myristate, making thereby a mixed carrier liquid. Antiperspirant properties and general physical properties are substantially the same as those of the above.

Additional preparations similar to the above are prepared which contain as antiperspirant 3.5% aluminum chlorhydroxide substituted for 7.0% aluminum chlorhydroxide. The mixed propellant is reduced from 83.9% to 80.4%. General physical properties are good.

Other compositions similar to the above are perpared which contain as antiperspirant 2% and 12% aluminum chlorhydroxide respectively. In each case the quantity of mixed propellant is adjusted correspondingly. Antiperspirant effectiveness and general physical properties are good.

When in the above examples the following complexes are substituted for the aluminum chlorhydroxide, substantially equivalent results are obtained in that the compositions are good antiperspirant compositions and the antiperspirant powder is suspended.

Complex I is prepared by the following procedure:

15.0 parts by weight of aluminum hydroxychloride (50% aqueous solution) was added to a beaker. Glycine was then added in an amount of 2.0 parts by weight and dissolved with the aid of a suitable mixer. Zirconyl hydroxychloride (33⅓% aqueous solution) was then added and mixed in an amount of 13.8 parts by weight. The combined components were then mixed until co-dissolved. The co-dissolved solution was then dried in an oven at a temperature of about 120° C. until a moisture content of 3% was attained. The dried solution now in a solid state was then placed into a ball mill and milled for about four hours which resulted in a fine powder. The powder was then passed through a 325 mesh screen to obtain a uniform size product.

Complex II is prepared as follows:

155 grams of a solution (50% nominal concentration) of aluminum chlorhydroxide (ACH) in water is heated in a suitable container to raise the temperature to 190° F. (The solution is agitated during the heating, utilizing suitable agitating means.) About ⅓ of 138 grams of a solution (33⅓ nominal concentration) of zirconyl hydroxychloride (ZHC) in water is then added in bulk to the ACH solution; and the remainder of the ZHC solution is added to the ACH solution in small portions over a period of 3 hours, the heating and agitation being continued during this period, and for about 3 hours after all the ZHC has been added. The heating and agitation is then stopped and the resulting aqueous complex (41% nominal concentration) is allowed to cool. The aqueous solution is subsequently dried in an oven at a temperature of 140° C. until a moisture content of about 5% is attained. The dried solution, now in a solid state, is then placed into a ball mill and milled for about 4 hours, giving a fine powder. The powder is then passed through a 325 mesh screen to obtain a uniform size product.

What is claimed is:

1. A powder aerosol antiperspirant composition comprising:
  A. from about 2% to about 12% by weight of a finely divided dry antiperspirant powder selected from the group consisting of aluminum chlorhydroxide and complexes of aluminum chlorhydroxide and zirconyl hydroxychloride;
  B. from about 0.2% to about 1% by weight of a suspending agent for the antiperspirant powder comprising a primary aliphatic amine having from about 12 to about 20 carbon atoms;
  C. from about 3% to about 15% by weight of a non-toxic, non-aqueous carrier liquid of low volatility having emollient properties, said liquid being selected from the group consisting of lanolin, polysiloxanes of the formula $(-R_2^5Si\,O-)_n$ wherein $R^5$ is $C_1-C_4$ alkyl or phenyl and wherein said polysiloxanes have a viscosity at 25° C. of from 5 to about 2,000 centistokes, polyalkylene glycols containing a fatty acid or fatty alcohol group containing from about 2 to about 20 carbon atoms, fatty alcohols containing from about 12 to about 18 carbon atoms, fatty acid esters of aliphatic alcohols wherein said esters contain from about 12 to about 26 carbon atoms, mineral oil having a specific gravity of from about 0.8 to about 0.9 at 60° F., aliphatic hydrocarbons containing from about 12 to about 26 carbon atoms, multiple ester organic compounds of from about 12 to about 16 carbon atoms having a ratio of ester groups to carbon atoms of from about 0.125 to about 0.214 and having a solubility in water of from about 0.0005% to about 0.1% at 30° C., and mixtures thereof; and
  D. from about 70.7% to about 93.9% by weight of an anhydrous, non-toxic, liquefiable propellant gas, under pressure.

2. The composition of claim 1 wherein component (B) comprises from about 0.3% to about 0.8% by weight of hexadecyl or octadecyl amine; and component (C) comprises from about 6% to about 10% by weight of isopropyl myristate, isopropyl palmitate, di-n-butyl phthalate, or diisopropyl adipate.

3. The composition of claim 2 wherein present are components (A), (B), (C), and (D), and in addition:
  E. from 0% to about 0.5% by weight of trichlorocarbanilide, hexachlorophene, trifluoromethyl carbanilide, or tribromosalicylanilide; and
  F. from 0% to about 0.8% by weight of perfume.

4. The powder aerosol antiperspirant composition of claim 1 wherein the amine is a saturated straight chain primary aliphatic amine.

* * * * *